United States Patent
Plaian et al.

(10) Patent No.: US 10,070,785 B2
(45) Date of Patent: Sep. 11, 2018

(54) EYE EXAMINATION APPARATUS

(71) Applicant: CENTERVUE S.P.A., Padua (IT)

(72) Inventors: Andrei Plaian, Ponte San Nicolò (IT); Irene Mogentale, Due Carrare (IT)

(73) Assignee: Centervue S.p.A., Padua (IT)

( * ) Notice: Subject to any disclaimer, the term of this patent is extended or adjusted under 35 U.S.C. 154(b) by 0 days.

(21) Appl. No.: 15/510,007

(22) PCT Filed: Sep. 7, 2015

(86) PCT No.: PCT/EP2015/070385
§ 371 (c)(1),
(2) Date: Mar. 9, 2017

(87) PCT Pub. No.: WO2016/037980
PCT Pub. Date: Mar. 17, 2016

(65) Prior Publication Data
US 2017/0251918 A1 Sep. 7, 2017

(30) Foreign Application Priority Data
Sep. 12, 2014 (IT) .............................. TV2014A0130

(51) Int. Cl.
*G02C 5/00* (2006.01)
*A61B 3/12* (2006.01)
(Continued)

(52) U.S. Cl.
CPC .............. *A61B 3/12* (2013.01); *A61B 3/0008* (2013.01); *A61B 3/1025* (2013.01); *A61B 3/15* (2013.01); *G02B 5/005* (2013.01)

(58) Field of Classification Search
CPC ....... A61B 3/12; A61B 3/1025; A61B 3/0008; A61B 3/15; G02B 5/005
(Continued)

(56) References Cited

U.S. PATENT DOCUMENTS 5,713,047 A 1/1998 Kohayakawa
5,847,805 A 12/1998 Kohayakawa et al.
(Continued)

FOREIGN PATENT DOCUMENTS

CN 103767674 A 5/2014
EP 2106741 A1 10/2009
(Continued)

OTHER PUBLICATIONS

International Search Report: European Patent Office for PCT/EP2015/070385 dated Oct. 19, 2015 (dated Oct. 29, 2015).
(Continued)

*Primary Examiner* — Tuyen Tra
(74) *Attorney, Agent, or Firm* — Patterson Intellectual Property Law, P.C.; Gary L. Montle

(57) ABSTRACT

An eye examination apparatus comprises an illuminator adapted to project a light beam on an optical illumination path along a first optical axis to illuminate the retina of an eye, said illuminator comprising a light source and a projection diaphragm adapted to shape the light beam, during the operation of said examination apparatus said projection diaphragm being optically conjugated with the retina. Acquisition means receive light reflected by the retina and acquire images of the retina. Scanning means move the light beam projected on the surface of the retina along a scanning direction. Separation means of the beams separate the light projected by said illuminator from the light reflected by the retina. The projection diaphragm comprises a projection opening having an elongated shape and variable width, said projection opening comprising a portion having a width larger than the width of said projection opening at the first optical axis.

20 Claims, 7 Drawing Sheets

(51) Int. Cl.
 *A61B 3/10* (2006.01)
 *A61B 3/15* (2006.01)
 *A61B 3/00* (2006.01)
 *G02B 5/00* (2006.01)

(58) Field of Classification Search
 USPC .................................. 351/41, 200, 205, 206
 See application file for complete search history.

(56) References Cited

U.S. PATENT DOCUMENTS

| | | | |
|---|---|---|---|
| 8,517,536 B2 * | 8/2013 | Chou | A61B 3/12 351/206 |
| 9,089,290 B2 * | 7/2015 | Umekawa | A61B 3/12 |
| 2005/0068497 A1 | 3/2005 | Hanebuchi et al. | |
| 2009/0244483 A1 | 10/2009 | Yoshino et al. | |
| 2010/0128221 A1 | 5/2010 | Muller et al. | |

FOREIGN PATENT DOCUMENTS

| | | |
|---|---|---|
| JP | H05337087 A | 12/1993 |
| JP | 2005095691 A | 4/2005 |
| TW | 201204314 A | 2/2012 |
| WO | 2007142960 A2 | 12/2007 |

OTHER PUBLICATIONS

State Intellectual Property Office of the People's Republic of China: Notification of First Office Action (PCT Application in the National Phase), Application No. 201580061474.X, dated May 28, 2018, 13 pages.

\* cited by examiner

EYE EXAMINATION APPARATUS

BACKGROUND OF THE INVENTION

The present invention relates to an eye examination apparatus.

The apparatus according to the invention is preferably used in ophthalmology to acquire images of the retina. In general, however, it can be used to acquire images of any object.

The use of apparatus for eye examination, commonly defined with the term "fundus cameras", is widely known. In general, these apparatus illuminate the whole of the retina with a flash of white light and acquire the light reflected by the retina to produce color photographs of this latter.

Usually, apparatus of this type, operating with the pupil not ciliated (non-mydriatic), are capable of photographing a relatively limited portion of the retina, corresponding to a maximum field of view of 45°, in conditions with pupil diameters of at least 4 mm. Some apparatus are also able to produce infrared videos and photographs.

The images (color or infrared) that can be obtained by illuminating the whole retina simultaneously are typically characterized by low contrast, due to the partial transparency of the retina. This drawback is more pronounced in the case of infrared videos or photographs.

Eye examination confocal apparatus are known. These apparatus can produce photographs and videos of the retina with good contrast and field of view greater than 45° (also in conditions with pupil diameters of less than 4 mm). There are two types of known confocal apparatus, i.e. the point scanning type and the line scanning type. For reasons of simplicity of construction, confocal line scanning apparatus are of particular industrial and commercial interest.

Examples of confocal line scanning apparatus are described in the patent documents U.S. Pat. No. 4,241,257, U.S. Pat. No. 7,331,669 and EP2392915A1.

These apparatus scan the retina with a light beam that illuminates a very narrow region of the retina, typically in the form of a line. They collect and de-scan the light reflected by the retina, passing it through a fixed diaphragm in slit form that eliminates most of the spurious light coming from undesired reflections. The light passing through the diaphragm is then projected on a sensor, by means of which one or more images of the retina are acquired.

An important drawback of confocal line scanning apparatus consists in that they require illumination sources with high radiance to obtain satisfactory illumination power to acquire the photos. Consequently, the light sources typically used consist of lasers, superluminescent diodes (SLD) or the like. These light sources are generally monochromatic or have a limited light emission band. For this reason, these apparatus are capable of supplying high contrast retinal images only with infrared or monochromatic visible light.

Some apparatus are also able to supply color images of the retina by combining monochromatic images obtained used red, green and blue lasers as light sources. However, the color images thus obtained do not offer the same degree of detail and natural color tones as images obtainable with an examination apparatus that uses a light source capable of emitting white light.

Examples of confocal line scanning apparatus that use white light sources have been proposed. However, due to insufficient radiance of the available white light sources, the solutions proposed to date have not led to mass-produced commercial products.

The apparatus in the U.S. Pat. No. 7,331,669 describes a digital photographic system that scans the retina with the light generated by an illuminator containing a diaphragm in the shape of a slit to reduce undesired reflections. In one of the construction variants proposed, the light reflected by the retina is de-scanned, passed through a confocal diaphragm that eliminates reflections and then rescanned to be projected on a two-dimensional sensor.

The photographic system described in this patent document does not provide practical solutions to improve, in a satisfactory manner, the transfer of power from the light source to the retina, so as to enable the use of low radiance white light sources, such as LED devices or the like. Consequently, the two-dimensional sensor must have a high gain during acquisition. This often causes the images acquired to be noisy, above all at the edges.

The increased exposure time using a slow scan, as proposed in the U.S. Pat. No. 7,331,669, improves the signal/noise ratio of the images. However, this solution increases the risk of movement of the eye during acquisition of the images, with the possible consequent presence of movement artefacts and blurring.

The patent application WO2009004497A2 proposes a white light apparatus provided with a linear source produced as an incandescent wire or a strip of LEDs, suitably arranged. The solution proposed for the shape of the light source does not solve the problem of insufficient radiance of this latter. Therefore, it does not cause an increase in the light power transmitted in the region of the retina (in the form of a line) that is illuminated.

A further drawback of prior art confocal line scanning apparatus consists in the fact that they do not typically allow photographs with sufficiently uniform distribution of brightness to be obtained, above all in the case of images corresponding to fields of view greater than around 30°.

It is known how common LED or laser diode devices emit light with generally non-uniform power distribution, variable as a function of the light emission angle. The power density of these light sources is usually greater along the optical axis and progressively decreases toward the periphery of the light emission cone. This behavior makes it difficult to construct a collimating optics of the light source that supplies an output light beam having uniform power density.

It must also be considered that the retina of the eye typically has reflectivity variable as a function of the illumination angle and type of light used for illumination (e.g. white or infrared). This makes the distribution of brightness in the images of the retina even more non-uniform.

Any correction of an image acquired with non-uniform light distribution via software worsens the signal/noise ratio in the regions characterized by low brightness. This reduces the quality of the images due to the increase in noise, making the images of little use for medical diagnosis.

In prior art examination apparatus of the line scanning type, one of the most widely used solutions to reduce reflections caused by the cornea and lens of the eye is to create a separation of the "side-by-side" type of the illumination light beam entering the eye with respect to the beam of light reflected by the retina and used by the apparatus to create the image of the retina. This solution has considerable advantages in terms of simplicity of construction and allows good quality images to be obtained for fields of view up to around 30°.

If images with greater fields of view, for example of around 60°, are required, the fact of having light beams passing through different regions of some lenses of the apparatus causes different distortions in the aforesaid light beams, preventing the line of light projected on the retina to be optically conjugated, for the whole of its length, with the confocal diaphragm. This causes a loss of brightness or the appearance of dark regions toward the outer edges of the images.

Further examples of eye examination apparatus are disclosed in patent documents U.S. Pat. No. 5,847,805 and US2005/068497.

BRIEF SUMMARY OF THE INVENTION

The main aim of the present invention is to provide an eye examination apparatus, of confocal line scanning type, which solves the aforesaid problems of the prior art.

Within this aim, an object of the present invention is to provide an eye examination apparatus that allows maximization of the light power transmitted by the illuminator, especially in the peripheral regions of the retina examined where there is normally a lack of light.

A further object of the present invention is to provide an eye examination apparatus that is capable of acquiring images of the retina with a relatively wide field of view.

Another object of the present invention is to provide an eye examination apparatus that allows a reduction in light disturbances caused by reflections of the illumination light on its constituent parts (for example lenses or mechanical parts).

A further object of the present invention is to provide an eye examination apparatus capable of producing high contrast, infrared, color, red-free, fluorescence or autofluorescence videos and photographs of the retina.

A further object of the present invention is to provide an eye examination apparatus that is easy to produce on an industrial scale, at competitive costs.

This aim and these objects, together with other objects that will be more apparent from the subsequent description and from the accompanying drawings, are achieved according to the invention by an eye examination apparatus according to claim 1 and to the related dependent claims, proposed hereunder.

In a general definition thereof, the apparatus according to the invention comprises:
- at least an illuminator adapted to project a light beam on an optical illumination path, along a first optical axis, to illuminate the retina of an eye, said illuminator comprising at least a light source;
- acquisition means adapted to receive light reflected by the retina along an optical imaging path having a second optical axis and to acquire images of the retina;
- scanning means adapted to move the light beam projected by the illuminator on the surface of the retina along a scanning direction;
- separation means of the light beams adapted to separate the projected light by said illuminator from the light reflected by the retina and directed toward said acquisition means.

Said illuminator comprises at least a projection diaphragm adapted to shape the light beam projected by said light source toward the optical illumination path.

During the operation of said examination apparatus, said projection diaphragm is optically conjugated with the retina.

The aforesaid projection diaphragm comprises at least a projection opening having an elongated shape and variable width. This projection opening is shaped so as to have at least a portion of a width larger than the width of said projection opening at the optical axis of the illumination path. Preferably, said projection opening is shaped so that its width progressively increases with the distance from the first optical axis between a minimum value, at the first optical axis, and maximum values, at the ends of said projection opening or at portions of said projection opening that are proximate to these ends.

Preferably, said illuminator comprises at least a projection mask adapted to stop a portion of the light emitted by said light source. Said projection mask is optically conjugated with a region of said apparatus comprised between the scanning means and a separation diaphragm of the separation means of the beams.

Said projection mask comprises at least a rectilinear edge. The rectilinear edge of the projection mask defines the edge of the light beam projected by the illuminator along said optical illumination path, at the aforesaid region comprised between said separation means of the light beams and said scanning means.

Preferably, the light beam projected by the illuminator does not cross any portion of the separation diaphragm of the separation means of the beams in proximity of an opening of the separation diaphragm through which light reflected by the retina passes.

Preferably, said projection mask is positioned in the proximity of said light source.

Preferably, the apparatus according to the invention comprises, along said optical imaging path, a confocal diaphragm that allows the passage of a portion of the light reflected by the retina.

During the operation of said examination apparatus, said confocal diaphragm is optically conjugated with the retina.

Said confocal diaphragm comprises at least a confocal opening having an elongated shape and variable width. This confocal opening is shaped so as to have at least a portion of a width larger than the width of said confocal opening at the optical axis of the acquisition path.

Preferably, said confocal opening is shaped so that its width progressively increases with the distance from the second optical axis between a minimum value, at the second optical axis, and maximum values, at the ends of said confocal opening or at portions of said confocal opening proximate to these ends.

In a possible embodiment, the apparatus according to the invention comprises at least two separate illuminators. Each illuminator comprises at least a corresponding light source and a corresponding projection diaphragm, optically conjugated with the retina of the eye during the operation of said apparatus. Each projection diaphragm comprises at least a projection opening having an elongated shape and variable width. Each projection opening is shaped so as to have at least a portion of a width larger than the width of said projection opening at the optical axis of the illumination path.

Preferably, each projection opening is shaped so that its width progressively increases with the distance from the first optical axis between a minimum value, at the first optical axis, and maximum values, at the ends of said projection opening or at portions of said projection opening that are proximate to these ends.

Preferably, each illuminator comprises at least a corresponding projection mask, optically conjugated with a region of said apparatus comprised between the scanning means and a separation diaphragm of the separation means of the beams and provided with at least a rectilinear edge.

The rectilinear edge of each projection mask optically defines the edge of the light beam projected by the corresponding illuminator along said optical illumination path, at the aforesaid region comprised between the scanning means and a separation diaphragm of the separation means of the beams.

Preferably, the light beam projected by each illuminator does not cross any portion of the separation diaphragm in proximity of an opening of the separation diaphragm through which light reflected by the retina passes.

Preferably, each projection mask is positioned in proximity of a corresponding light source.

Preferably, the confocal diaphragm of the examination apparatus comprises a first and second confocal opening having an elongated shape and variable width.

Each confocal opening is shaped so as to have, when inserted in the optical imaging path, at least a portion of a width larger than the width of said confocal opening at the optical axis of the acquisition path.

Preferably, when inserted in the optical imaging path, each of the confocal openings is shaped so that its width progressively increases with the distance from said second optical axis, between a minimum value, at the second optical axis, and maximum values, at the ends of said confocal opening or at portions of said confocal opening that are proximate to these ends.

The confocal diaphragm is advantageously movable with respect to the optical imaging path so that the aforesaid confocal openings can be inserted/removed, one at a time, in/from the optical imaging path.

In a possible embodiment, the apparatus according to the invention comprises at least an illuminator provided with at least two light sources that emit light in different spectral bands.

BRIEF DESCRIPTION OF THE SEVERAL VIEWS OF THE DRAWINGS

Further characteristics and advantages of the eye examination apparatus according to the invention will be more apparent with reference to the description given below and to the accompanying figures, provided purely for explanatory and non-limiting purposes, wherein.

DETAILED DESCRIPTION OF THE INVENTION

Figure 1:
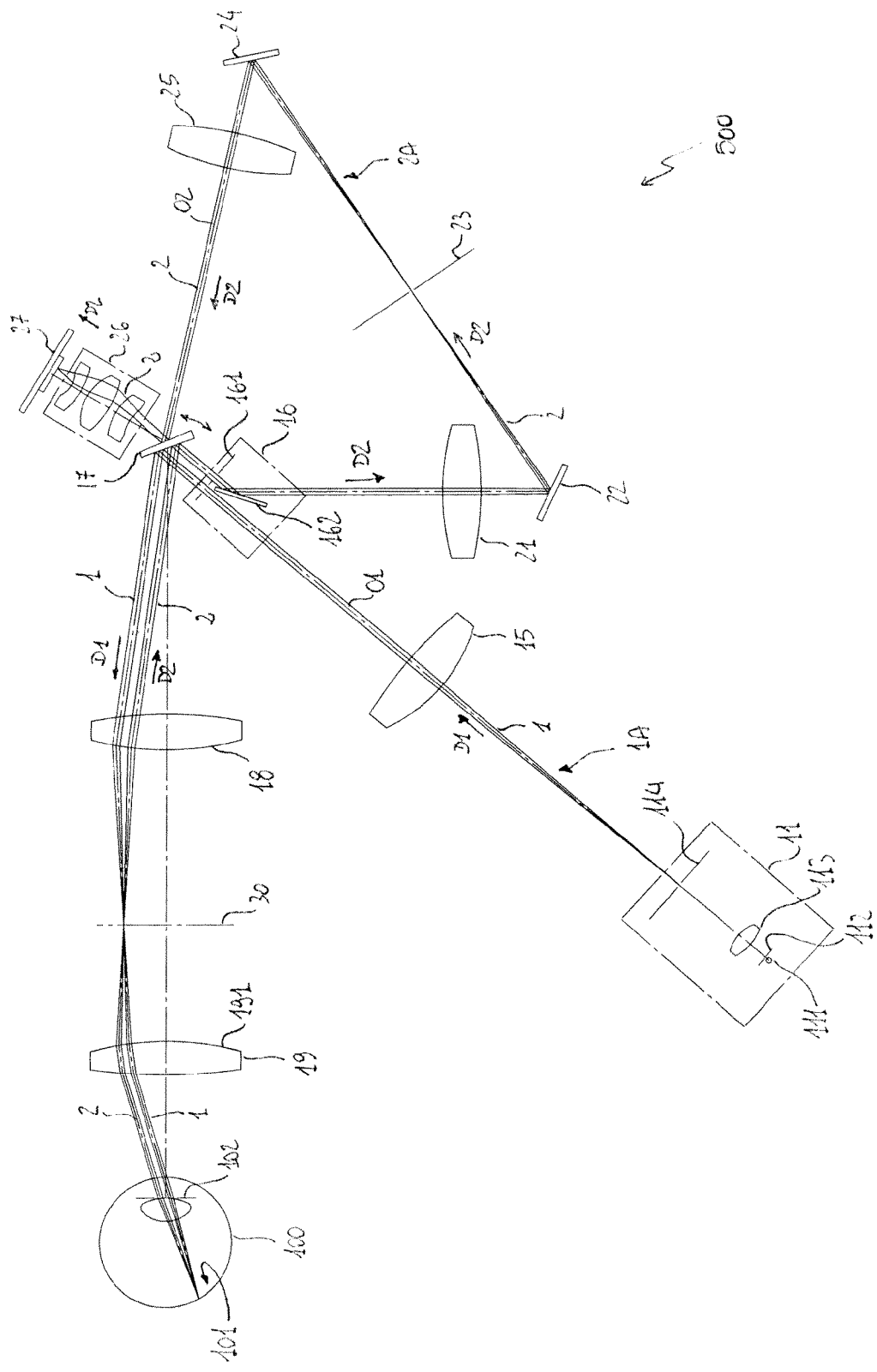
FIG. 1 schematically shows the eye examination apparatus according to the invention in a first embodiment thereof.

With reference to FIGS. 1-4, the present invention relates to an eye examination apparatus 500, in particular of confocal line scanning type. The apparatus 500 comprises a first illuminator 11 and an optical illumination path 1A having a first optical axis O1. Along the optical path 1A, a light beam 1 is projected in direction D1 by the illuminator 11 toward the retina 101 of the eye 100.

The apparatus 500 comprises acquisition means 27 adapted to receive light 2 reflected by the retina 101 and to acquire one or more images of the same retina.

The apparatus 500 comprises an optical imaging path 2A having a second optical axis O2. Along the optical path 2A, the light 2 reflected by the retina 101 travels in direction D2 until reaching the acquisition means 27.

The apparatus 500 comprises scanning means 17 adapted to move, along a scanning direction, the light beam 1 projected on the surface of the retina 101. Preferably, the scanning means 17 also have the function of directing at least a portion of the light 2 reflected by the retina along the optical imaging path 2A toward the acquisition means 27.

The apparatus 500 comprises separation means of the light beams 16 adapted to separate the light 1 projected on the retina from light 2 reflected by this latter.

The illuminator 11, the separation means of the light beams 16 and the scanning means 17 are arranged in series along the optical path 1A (with reference to the direction D1 of the light beam 1).

Preferably, the apparatus 500 comprises a first optics 15 arranged along the optical path 1A between the illuminator 11 and the separation means 16 of the light beams.

Preferably, the apparatus 500 comprises a scanning optics 18 and an eyepiece 19, arranged downstream of the scanning means 17 (with reference to the direction of travel D1 of the light beam 1) so as to be passed through by the illumination light 1.

The scanning means 17, the separation means of the light beams 16 and the acquisition means 27 are advantageously arranged in series along the optical path 2A (with reference to the direction of travel D2 of the light beam 2). The eyepiece 19 and the scanning optics 18 are passed through by the reflected light 2, before this latter reaches the scanning means 17.

Preferably, the apparatus 500 comprises a confocal diaphragm 23 arranged along the optical path 2A. As will be more apparent below, the confocal diaphragm 23 preferably comprises at least a suitably shaped confocal opening 231. This latter allows the passage of a portion of the light 2 reflected by the retina and at least partially stops the light reflected by some surfaces of the apparatus 500 or of the eye 100 that are not optically conjugated with the retina.

Preferably, the apparatus 500 also comprises a second optics 21, the mirrors 22, 24, a third optics 25, an objective 26 arranged along the optical path 2A, between the separation means of the beams 16 and the acquisition means 27.

The illuminator 11 comprises at least a first light source 111, preferably consisting of an LED (Light Emitting Diode) device.

The illuminator 11 comprises a first projection diaphragm 114 adapted to shape the light beam 1 projected by the light source 111 toward the optical path 1A.

The projection diaphragm 114 is arranged so as to be optically conjugated with the retina 101, during the operation of the apparatus 500.

For greater clarity of exposition, it is specified that, within the scope of the present invention, the definition "optically conjugated" identifies positioning in the exact position of optical conjugation or in a relatively small neighborhood (with respect to the lengths of the optical paths of the apparatus 500) of the exact position of optical conjugation.

As will be more apparent below, the projection diaphragm 114 comprises a first projection opening 1140 suitably shaped to shape the light beam projected by the light source 111 toward the optical path 1A.

Preferably, the illuminator 11 comprises a first projection mask 112 arranged so as to be optically conjugated with a region of the apparatus 500 comprised between the scanning means 17 and the separation means of the beams 16. During the operation of the apparatus 500, the projection mask 112 is optically conjugated with the pupil 102 of the eye. As will be more apparent below, the projection mask 112 is suitably shaped to stop a portion of the light emitted by the light source 111.

Preferably, the projection mask 112 is positioned in proximity of the light source 111.

Preferably, the illuminator 11 comprises a first collimating optics 113, positioned between the projection mask 112 and the projection diaphragm 114.

Preferably, the acquisition means 27 consist of, for example, CCD or C-MOS sensors of a digital video camera. They receive the light 2 at a receiving surface and allow the retina 101 to be observed and filmed.

Preferably, the separation means of the light beams 16 comprise a separation diaphragm 161, optically conjugated with the pupil 102, during the operation of the apparatus 500.

Preferably, the separation diaphragm 161 comprises shaped openings 161A, 161B for passage of the illumination light beam 1 and of the beam of reflected light 2, respectively. For the separation diaphragm 161 other configurations are possible as long as they provide for the presence of at least an opening 161B for the passage of a portion of the reflected light 2.

Preferably, the separation means of the light beams 16 comprise a mirror 162 adapted to divert the reflected light 2 directed by the scanning means 17 along the optical path 2A.

Other construction variants that provide for the use of beam splitters, mirrors or diaphragms having configurations different from the one shown in the aforesaid figures are possible.

Preferably, the scanning means 17 comprise a resonant oscillating mirror with two opposed reflecting surfaces. Other construction solutions for the scanning means 17 that, for example, provide for the use of a polygonal mirror, an array of micro mirrors or the like, are possible.

Preferably, the confocal diaphragm 23 is arranged so as to be optically conjugated with the retina 101, during the operation of the apparatus 500.

The general operation of the apparatus 500 is now described in greater detail.

The light emitted by the light source 111 is partially stopped by the mask 112, is collimated by the collimating optics 113 and passes through the diaphragm 114.

The light 1 projected by the illuminator 11 passes through the optics 15 and the separation means 16 of the light beams, in particular at the opening 161A of the separation diaphragm 161. Preferably, the light beam 1 does not touch any portion of the separation diaphragm 161 in proximity of the opening 161B through which light reflected by the retina passes. In particular, the light beam 1 does not touch the edges of the opening 161A.

The light 1 is scanned by the scanning means 17 that direct it toward the retina 101 moving around the rotation axis thereof. It passes through the scanning optics 18 and the eyepiece 19 and enters the eye 100 to illuminate the retina 101.

On the retina 101, the illuminated region consists of the light image of the opening 1140 of the projection diaphragm 114. This illuminated region moves along the retina according to a scanning direction established by the scanning means 17, which is substantially perpendicular to the direction of maximum extension of the illuminated region. As will be more apparent below, the illuminated region of the retina consists of a suitably shaped luminous linear region.

The retina 101 at least partially reflects the illumination light 1. The light 2 reflected by the retina 101 exits from the eye through the pupil 102 passes back through the eyepiece 19 and the scanning optics 18.

The reflected light 2 is de-scanned by the scanning means 17 that direct it along the optical path 2A.

The reflected light 2 passes through the separation means 16 of the light beams, in particular at the opening 161B of the separation diaphragm 161.

The separation means 16 of the light beams (in particular the separation diaphragm 161) select, by means of the opening 161B, the portion of reflected light 2 that passes through a predetermined region of the pupil 102 separated from the region of pupil through which the light beam 1 enters the eye. This greatly reduces the probability of undesired reflections of the illumination light 1, coming from other surfaces of the eye, reaching the acquisition means 27.

The light beam 2, selected by the separation means 16, passes through the optics 21, is reflected by the mirror 22, passes through the confocal diaphragm 23, is reflected by the mirror 24 and passes through the optics 25. Passage of the light beam 2 through the confocal diaphragm 23 greatly reduces the probability that undesired reflections, which come from objects positioned in planes different from the retina 101 or optically conjugated with the same retina, reach the acquisition means 27.

The light beam 2 is once again scanned by the scanning means 17 and directed toward the acquisition means 27.

The light beam 2 passes through the objective 26 to generate a two-dimensional image of the retina 101 on the receiving surface of the acquisition means 27 that acquire one or more images of said retina.

According to the invention, the projection diaphragm 114 comprises at least a first projection opening 1140. The projection opening 1140 has an elongated shape and variable width.

Preferably, the projection opening 1140 extends along the main axis of extension 1144.

Preferably, the projection diaphragm 114 is arranged so that the axis of extension 1144 of the opening 1140 crosses the optical axis O1 of the optical path 1A.

The projection opening 1140 comprises the ends 1142, in distal position with respect to the optical axis O1, and a central portion 1145, in proximate position with respect to the optical axis O1.

Preferably, the projection opening 1140 is centered on the optical axis O1.

Preferably, the ends 1142 are arranged symmetrically with respect to the central portion 1145.

According to the invention, the projection opening 1140 is shaped so as to have at least a portion of width larger than its width at the optical axis O1. In other words, the projection opening 1140 is shaped so that its width, at the central portion 1145, is smaller than its width at least at a different portion of the same opening.

Preferably, the projection opening 1140 is shaped so that its width progressively increases (i.e. moving away from the optical axis O1 along the axis 1144), between a minimum value, at the optical axis O1, and maximum values, at the ends 1142 or portions proximate to the ends 1142.

Regions proximate to the ends 1142 (and not necessarily only the ends 1142) have been considered given that, at the aforesaid portions, the shape of the opening 1140 can be altered by connections of the edges of the same opening or given that the length of the opening 1140 can be increased to compensate for assembly errors.

Preferably the width $l_1$ of the projection opening 1140 varies with the distance $x_1$ with respect to the optical axis O1 according to a law of variation $l_1=f1(x_1)$ such as to make the brightness of the image of the retina 101 acquired with the acquisition means 27 more uniform.

Figure 3:
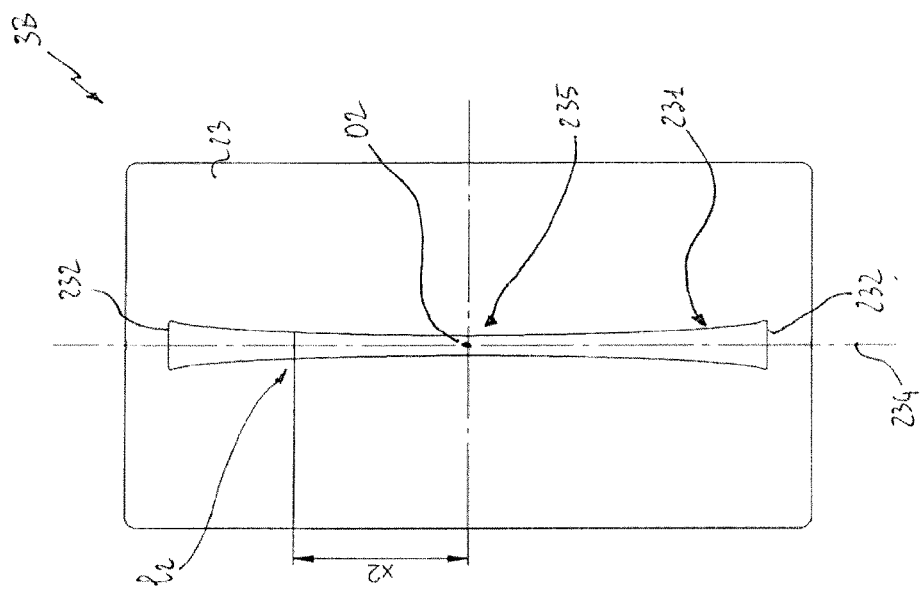
Figure 3:
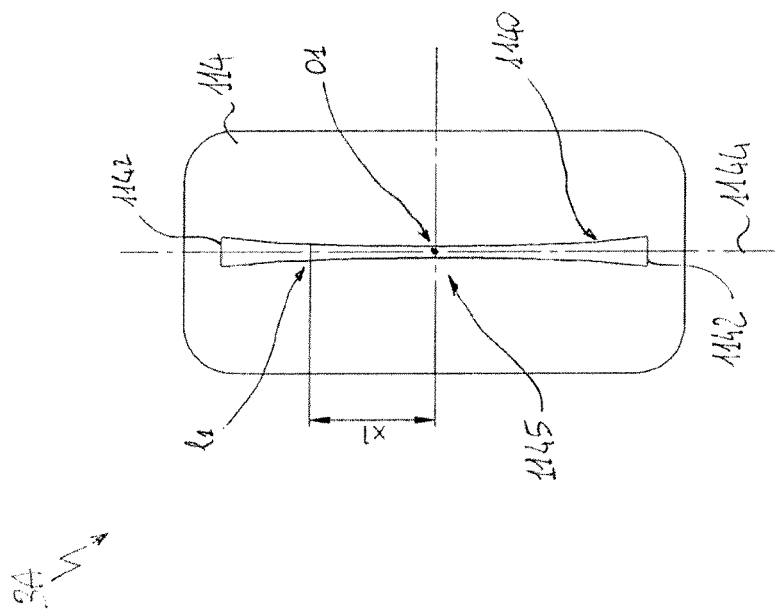

An example of embodiment of the opening 1140 of the projection diaphragm 114 is shown in FIG. 3 (view 3A). Given the particular shape of the projection opening 1140, the illuminated region on the retina 101, represented by the light image formed by the opening 1140, has substantially the shape of a line of light. This line of light has a width variable between a minimum value, at a central portion thereof, and a maximum value, at least at a different region of the central portion. Due to the action of the scanning means 17, this line of light moves along the surface of the retina 101, according to a scanning direction perpendicular to the same line.

According to an embodiment of the invention, the confocal diaphragm 23 preferably comprises at least a confocal opening 231 having an elongated shape and variable width.

Preferably, the confocal opening 231 extends along a main axis of extension 234.

Preferably, the confocal diaphragm 23 is arranged so that the axis of extension 234 of the opening 231 crosses the optical axis O2 of the optical path 2A.

The confocal opening 231 comprises the ends 232, in distal position with respect to the optical axis O2, and a central portion 235, in proximal position with respect to the optical axis O2.

Preferably, the confocal opening 231 is centered on the optical axis O2.

Preferably, the ends 232 are arranged symmetrically with respect to the central portion 235.

Preferably, the confocal opening 231 is shaped so as to have at least a portion of a width larger than the width of said confocal opening at the optical axis O2. In other words, the confocal opening 231 is shaped so that its width, at the central portion 235, is smaller than its width at least at a different portion of the same opening.

Preferably, the confocal opening 231 is shaped so that its width progressively increases with the distance from the optical axis O2 (i.e. moving away from the optical axis O2 along the axis 234), between a minimum value, at the optical axis O2, and maximum values, at the ends 232 or at portions proximate to the ends 232.

Preferably, the width $l_2$ of the confocal opening 231 varies with the distance $x_2$ with respect to the optical axis O2, according to a law of variation $l_2=f2(x_2)$ such as to make the brightness of the image of the retina 101 acquired with the acquisition means 27 more uniform.

An example of embodiment of the opening 231 of the confocal diaphragm 23 is shown in FIG. 3 (view 3B). The particular shaping of the opening 1140 of the projection diaphragm 114 and of the opening 231 of the confocal diaphragm 23 has considerable and surprising advantages. The brightness of the images of the retina 101 is made more or less uniform due to the simultaneous contribution of the profiles of the openings 1140 and 231.

The smaller width of the openings 1140, 231, at the respective central regions 1145 and 235, makes it possible to compensate for the greater power density in axial direction that characterizes light sources currently available on the market, for example LED, laser diode, superluminescent diode devices or the like.

Conversely, the larger width of the openings 1140, 231, at regions different from the central region, makes it possible to compensate for the lower power density of the light source 111 in emission directions different from the axis of the same source and the characteristic variations of reflectivity of the retina 101 as a function of the angle between the light beam 1 and the optical axis of the eye, which are known to be more favorable for central light beams and less favorable for peripheral light beams.

Figure 4:
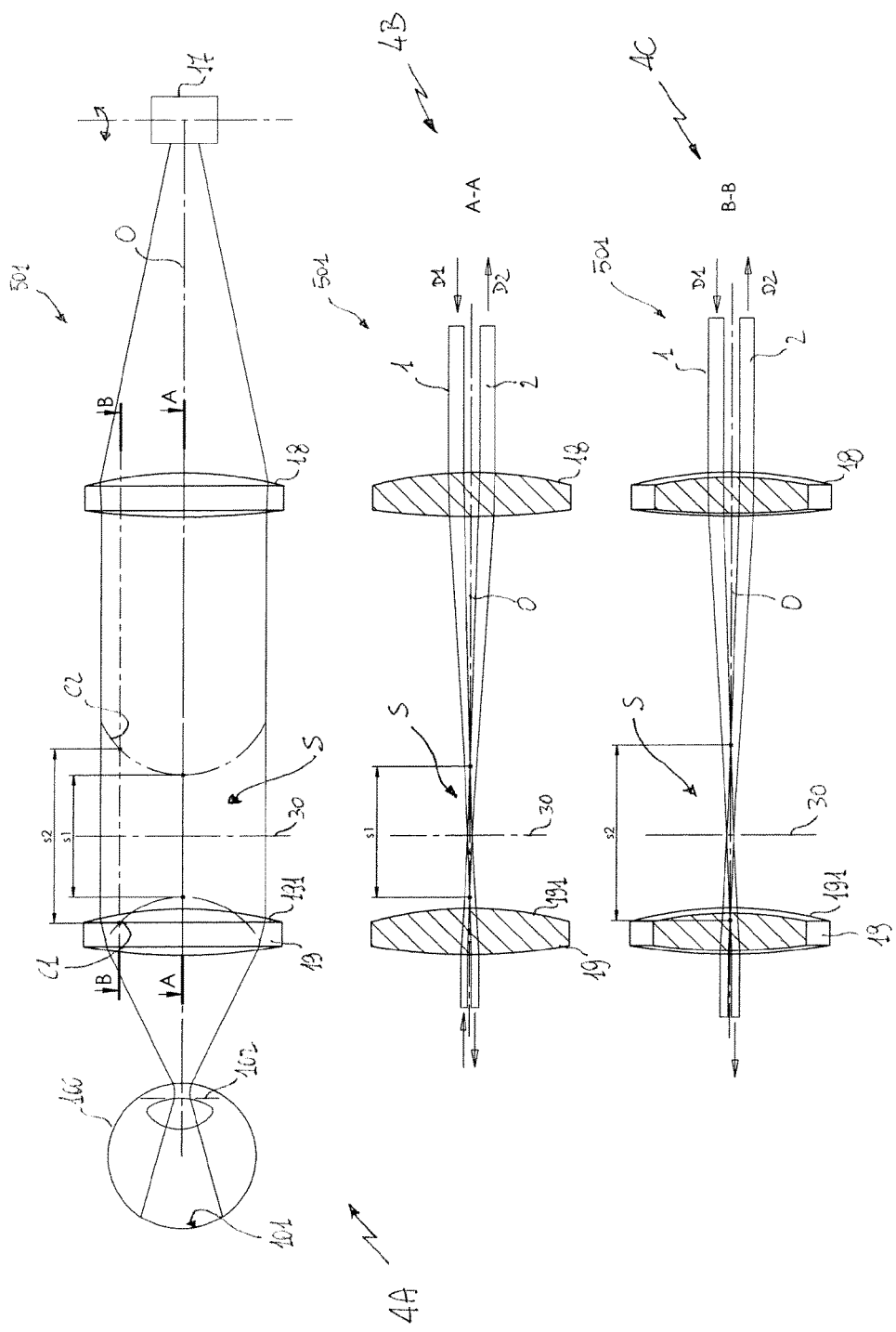

FIG. 4 (views 4A-4C) shows in greater detail the portion 501 of apparatus 500 that, during the operation of the same apparatus, is operatively positioned between the scanning means 17 and the eye 100. Both the illumination light 1 and the reflected light 2 travel through the portion of apparatus 501. At this portion, undesired reflections capable of entering the optical path 2A and causing disturbances to the image acquired by the acquisition means 27 can be generated.

In order for these undesired reflections to be able to reach the receiving surface of the acquisition means 27, two conditions must simultaneously occur:
  the surface that generates the undesired reflections must cross the overlapping region of the light beam 1 and the light beam 2;
  the surface that generates the undesired reflections must be more or less perpendicular to the common direction of the light beams 1 and 2.

The optical surface that can best satisfy both conditions, and that therefore has a greater probability of generating undesired reflections, is the surface 191 of the lens of the eyepiece 19 proximate to the surface 30 conjugated with the retina 101. The portion of surface 191 having the maximum probability of generating undesired reflections is the one in proximity of the related optical axis O given that it is the only one more or less perpendicular to the common direction of the beams 1 and 2.

The risk of undesired reflections further increases when a very short sighted eye 100 is photographed, as the surface 30 necessarily moves toward the surface 191 of the lens of the eyepiece 19.

The overlapping regions of the light beam 1 and the light beam 2 are centered with the retina 101 and with the surfaces optically conjugated therewith. These overlapping regions extend from one part and from the other part of the retina 101 or of the related optical conjugates on distances that depend on the widths of the same light beams at the retina or at the surfaces optically conjugated therewith.

The view 4A shows the boundary surfaces C1, C2 of the overlapping region S between the light beams 1 and 2.

FIG. 4 also shows a section A-A of the portion of apparatus 501 along a plane passing through the optical axis O (view 4B).

The overlapping region S between the light beam 1 and the light beam 2 extends more or less symmetrically from one part and from the other part of the surface 30 and has an amplitude s1 that depends on the central thicknesses (i.e. at the optical axis O) of the light beam 1 and of the light beam 2 that cross the surface 30.

The central thicknesses of the light beams 1, 2 are proportional to the width of the openings 1140, 231 of the diaphragms 114, 23 at the related central regions 1145, 235. When the width of the openings 1140, 231 of the diaphragms 114, 23, at the related central regions 1145, 235, reaches certain values, the overlapping region S between the light beams 1 and 2 touches the surface 191 in the neighborhood of the optical axis O. In this case, the light reflected by the surface 191 can enter the optical path 2A causing an undesired reflection on the image of the retina 101.

To avoid the appearance of undesired reflections, the overlapping region S must be maintained (in proximity of the optical axis O) at least at a minimum safety distance from the surface 191, as shown in the view 4B. Consequently, the width of each of the openings 1140, 231 of the diaphragms 114, 23, at the related central regions 1145, 235, must remain below a corresponding maximum value to prevent the formation of undesired reflections coming from the surface 191 of the eyepiece 19.

FIG. 4 also shows a section B-B of the portion of apparatus 501 along a plane different from the optical axis O and relatively distant from this latter (view 4C). The overlapping region S between the light beams 1 and 2 crosses the surface 191 at lengths of surface distant from the optical axis O. The rays of light (of the light beam 1) distant from the optical axis O, for example passing in proximity of the ends 1142 of the opening 1140 of the diaphragm 114, meet the spherical surface 191 in peripheral regions of this latter, at which the surface 191 is greatly inclined with respect to the same rays of light.

The illumination rays incident on these peripheral regions are reflected in lateral directions and do not risk entering the optical path 2A to cause undesired reflections. Consequently, in the regions distant from the optical axis O, the light beams 1 and 2 can have relatively large thicknesses and consequently generate an overlapping region S that can also cross the surface 191 without the danger of undesired reflections. Therefore, the width of each of the openings 1140, 231 of the diaphragms 114, 23, at portions different from the central portions 1145, 235, can be larger than the width, at the same related central regions 1145, 235 without causing undesired reflections.

Based on the above, to avoid undesired reflections on the image there must be a minimum distance along the axis between the overlapping region S and the surface 191 of the lens at the optical axis O. This necessary minimum distance progressively decreases moving away from the optical axis O.

It is also possible for the overlapping region S to penetrate the lens of the eyepiece 19 at peripheral regions of the surface 191 without causing undesired reflections.

The width of each of the openings 1140, 231 of the diaphragms 114, 23 can thus advantageously increase moving away from the respective optical axes O1, O2 without causing the occurrence of undesired reflections.

The particular shaping of the openings 1140, 231 of the diaphragms 114, 23, described above, offers the surprising advantage of increasing the light power projected in the peripheral regions of the line of light that scans the retina, without causing undesired reflections. In this way it is possible to compensate for the characteristic lack of brightness in the peripheral regions of the images of the retina 101 that would emerge using diaphragms having rectangular openings, already described in the prior art.

The particular shaping of the openings 1140, 231 of the diaphragms 114, 23, described above, lead to further advantages, in the case in which the apparatus 500 is arranged to provide images with wide field of view, for example of around 60°.

In principle, the different distortions to which the light beams 1 and 2 are subjected, passing through different regions of the various lenses of the apparatus 500, make it difficult to optically conjugate the confocal diaphragm 23 with the line of light projected on the retina 101 for the whole length of the aforesaid line of light.

As already mentioned, in prior art apparatus, satisfactory optical conjugation is normally possible for fields of view up to around 30° while, for wider fields of view, the brightness of the images of the retina drastically worsens, above all at the peripheral regions, where the effect of the distortions is greater and, consequently, the conjugation between the line of light and the diaphragm 23 becomes less accurate.

The particular shaping of the openings 1140, 231 of the diaphragms 114, 23, described above, allows this criticality to be greatly reduced.

The variation of peripheral brightness of the photo can be easily compensated by suitably calculating the laws of variation of the width $l_1=f1(x_1)$ and $l_2=f2(x_2)$ that characterize the openings 1140, 231 of the diaphragms 114 and 23, respectively.

The solution proposed by the present invention thus allows images of the retina 101 of good quality to be obtained also on very wide fields of view.

This represents a considerable improvement of performances with respect to those offered by prior art apparatus, in which a line of light of constant width is projected and confocal diaphragms having openings in the shape of a rectangular slit are used.

As mentioned above, the illuminator 11 preferably comprises a first projection mask 112. The projection mask 112 is optically conjugated with a region of the apparatus 500 comprised between the scanning means and the separation means of the beams, in particular the diaphragm 161. During the operation of the apparatus 500 the projection mask 112 is optically conjugated with the pupil 102 of the eye 100. The projection mask 112 has the function of defining the shape of the section of the illumination beam 1 at the level of the region comprised between the diaphragm 161 and the scanning means 17 and consequently also at the level of the pupil 102.

The projection mask 112 comprises at least a rectilinear edge 1121.

Preferably, the rectilinear edge 1121 defines a clear boundary 1B of the section of the beam 1, at a region comprised between the separation means 16 and the scanning means 17.

Figure 2:
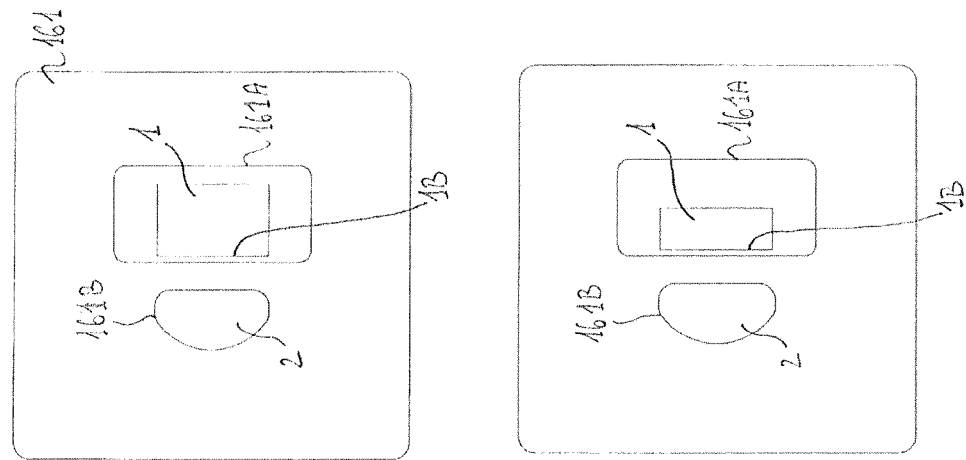
FIGS. 2-4 schematically show some details of the eye examination apparatus of FIG. 1.
Figure 2:
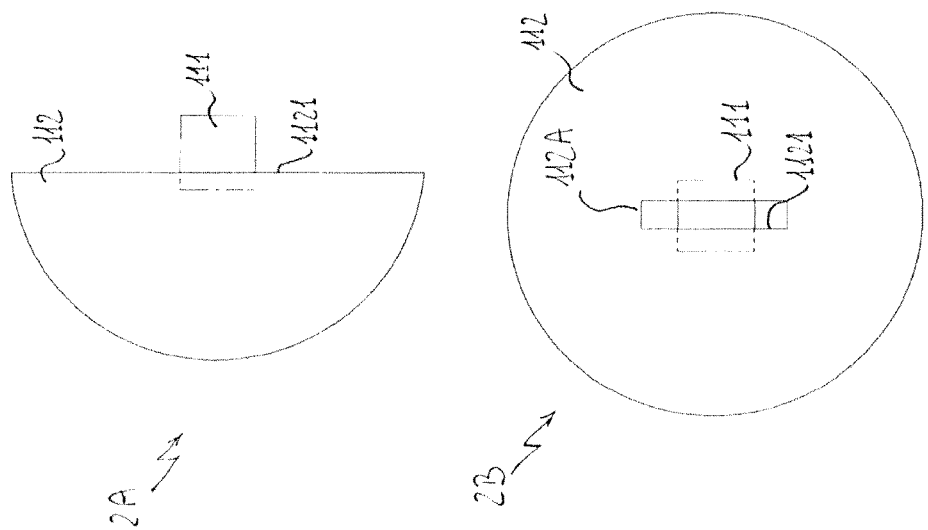

An embodiment for the projection mask 112 is shown in the view 2A of FIG. 2.

The projection mask 112 stops a portion of the light 1 emitted by the light source 111 and comprises a rectilinear edge 1121. The rectilinear edge 1121 is optically conjugated with the boundary 1B of the section of the light beam 1 at the region comprised between the separation diaphragm 161 of the separation means 16 and the scanning means 17.

The boundary 1B of the section of the light beam 1 defines, at the separation diaphragm 161, a clear passage between a region of high power density inside the light beam 1 and a dark region that separates the light beam 1 from the light beam 2. This ensures good separation between the light beams 1 and 2, which is necessary to prevent the light caused by reflections on various optical surfaces of the apparatus 500 or of the eye 100 from entering the optical path 2A and reaching the acquisition means 27, causing disturbances on the final image of the retina 101.

The projection mask 112 allows the above to be obtained without the light beam 1 being intercepted by portions of the separation diaphragm 16 in proximity of the opening 161B of the projection diaphragm 16.

It is prevented the occurrence of scattering phenomena at the separation means of the light beams 16, at which the optical paths 1A, 2A are proximate to each other. This constitutes a considerable advantage, given that the presence of any scattering phenomena at the separation means of the light beams 16 could easily cause undesired reflections on the image of the retina 101.

As mentioned above, the projection mask 112 is preferably positioned in proximity of the light source 11, upstream of the separation diaphragm 114 (with reference to the direction of travel D1 of the light beam 1).

In this way, the projection diaphragm 114 stops most of the light generated by scattering phenomena at the projection mask 112 and consequently eliminates the danger of undesired reflections.

A further embodiment for the projection mask 112 is shown in the view 2B of FIG. 2.

In this example, the light source 111 is relatively extended, for example a LED device.

The mask 112 comprises a through opening 112A (for example of rectangular shape) that comprises at least a rectilinear edge 1121 and also other edges, rectilinear or of different shape, that stop a portion of the light 1 emitted by the light source 111.

Also in this case, the rectilinear edge 1121 defines, at the level of the region comprised between the separation diaphragm 161 and the scanning means 17, a boundary 1B of the section of the light beam 1 that allows a clear region of separation between the light beams 1 and 2 to be obtained, without the light beam 1 touching any portion of the diaphragm 161.

In the example illustrated, the opening 112A is rectangular and is positioned in proximity of the light source 111.

The opening 112A has smaller width and larger length than the equivalent dimensions of the emitting surface of the emitter 111.

In this way, the section of the light beam 1, at the region optically conjugated at the level of the separation diaphragm 161 and at the pupil 102, is defined in one direction by the image of the edges of the opening 112A of the projection mask 112 and, in the other direction, by the image of the edges of the emission surface of the light source 111.

The solution proposed in the example 2B allows the whole section of the light beam 1 at the level of the pupil 102 to be defined as desired.

This can be useful to suitably decrease and shape the emission section of an LED device used as light source 111.

The projection mask 112 can be produced according to further configurations that are always characterized by the presence of at least a rectilinear edge 1121 capable of stopping a portion of the light emitted by the light source 111.

Figure 5:
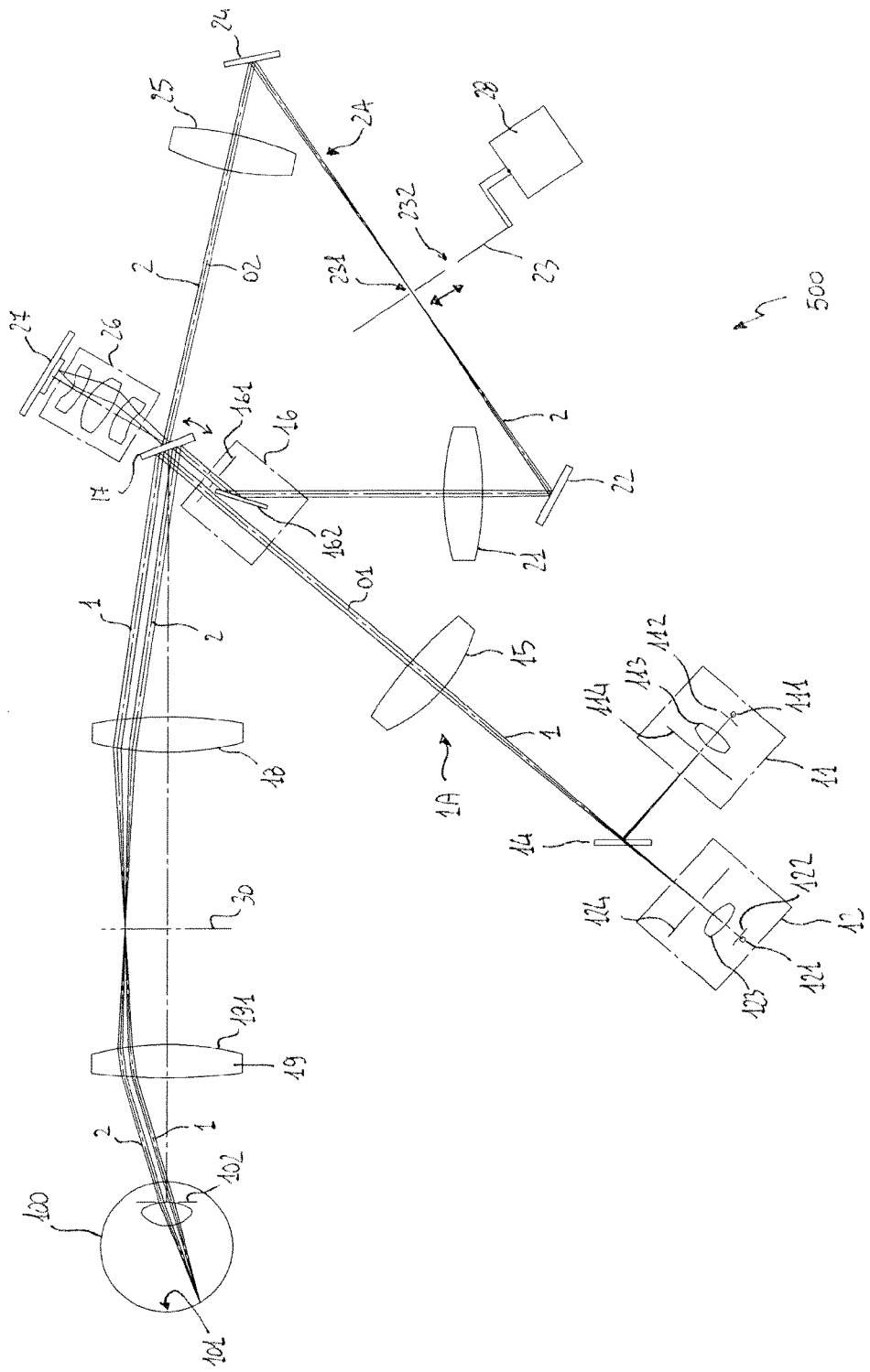
FIG. 5 schematically shows the eye examination apparatus according to the invention in a further embodiment thereof.
Figure 6:
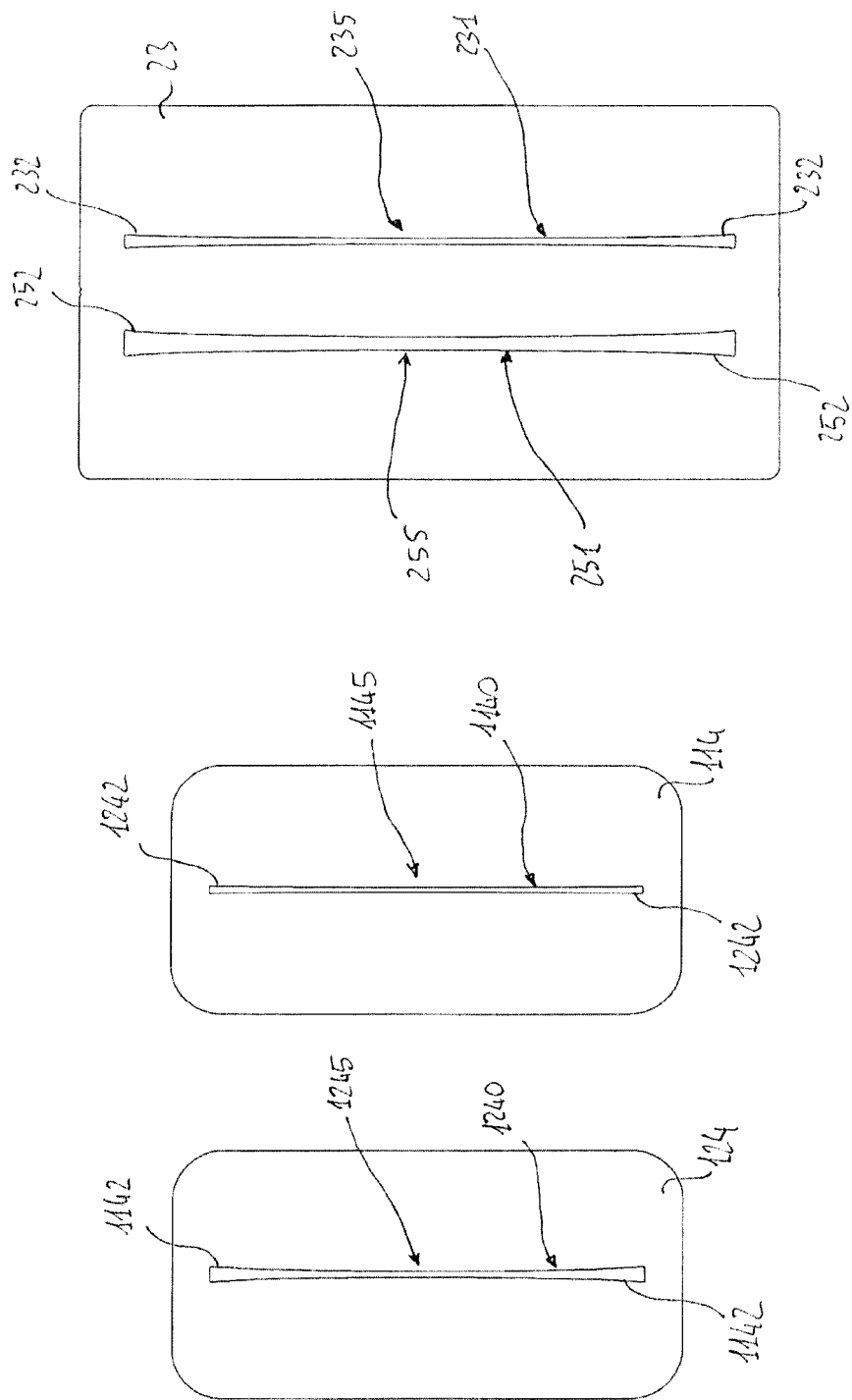
FIG. 6 schematically shows some details of the eye examination apparatus of FIG. 5.

FIGS. 5-6 show a further embodiment for the apparatus 500.

Many of the construction aspects of this embodiment of the apparatus 500 are substantially identical to the embodiment shown in FIGS. 1-4.

An important aspect of differentiation consists in that, in this embodiment, the apparatus 500 comprises two separate illuminators, in particular the first illuminator 11 and a second illuminator 12.

The apparatus 500 comprises a dichroic mirror 14 for coupling the illuminators 11, 12 on the same optical path 1A.

The illuminator 11 has substantially the same construction and the same operation as the illuminator 11 already described in relation to FIGS. 1-4.

In this case, it advantageously comprises an infrared light source 111, for example an infrared LED device.

The construction and operation of the illuminator 12 is very similar to the illuminator 11 already described in relation to FIGS. 1-4.

It comprises at least a second white-light light source 121, for example a white LED device or other broadband light source.

Moreover, it comprises a second projection diaphragm 124 produced in the same way as the first projection diaphragm 114 already described in relation to the first illuminator 11.

The projection diaphragm 124 comprises at least a second projection opening 1240 shaped similarly (even if not necessarily identically) to the first projection opening 1140 of the first projection diaphragm 114 (FIG. 6). The projection opening 1240 has an elongated shape and variable width and preferably extends along a corresponding main axis of extension.

Preferably, the projection diaphragm 124 is arranged so that this axis of extension crosses the optical axis O1.

The projection opening 1240 comprises corresponding ends 1242 in distal position with respect to the optical axis O1 and a corresponding central portion 1245 in proximal position with respect to said optical axis.

Preferably, the projection opening 1240 is centered on the optical axis O1.

Preferably, the ends 1242 of the projection opening 1240 are arranged symmetrically with respect to the central portion 1245.

The projection opening 1240 is shaped so as to have at least a portion of a width larger than its width at the optical axis O1. In other words, the projection opening 1240 is shaped so that its width, at the central portion 1245, is smaller than its width at least at a portion different from the central portion.

Preferably, the projection opening 1240 is shaped so that its width progressively increases with the distance from the second optical axis O1, advantageously according to a law of variation such as to make the brightness of the image of the retina 101 acquired by the acquisition means 27 more uniform.

The laws of variation of the width of the openings 1140, 1240 of the diaphragms 114 and 124 can differ from each other based on different calculation criteria.

It is known that infrared light penetrates the retina 101 more deeply than white light, which is reflected or diffused in a more superficial layer of the retina. This requires a more marked confocality (i.e. scanning of the retina with a narrow and well-focused line of light) in the case of use of infrared light to obtain images of the retina with sufficient contrast. This makes the choice of a narrower opening 1140 useful.

Instead, in the case of illumination with white light, optimization of the contrast of the image is not the main selection criterion of the width of the opening 1240. In this case, it is more advantageous to optimize the power projected on the retina through the opening 1240, given that the reflectivity of the retina with visible light is very low. This makes the choice of wider opening 1240 with respect to the opening 1140 used for the infrared light useful.

An increase in the width of the line of light with which the retina 101 is scanned allows an increase of the light power projected on the retina.

It has been seen that the increase in width of this line of light can be obtained up to a certain limit value, beyond which undesired reflections coming from surfaces different from the retina and its conjugates can be generated. It is therefore possible to optimize the quantity of light that can be projected on the retina 101 in conditions of absence of reflections. The law of variation of the width of the opening 1140 of the diaphragm 114 of the infrared illuminator 11 can therefore be optimized to obtain a good compromise between contrast and the brightness of the image.

On the other hand, the law of variation of the width of the opening 1240 of the diaphragm 124 can be optimized, in a differentiated manner, to obtain a good brightness of the image associated with the absence of reflections.

The confocality of the apparatus 500 in white light, even if it is more relaxed due to the larger width of the line of light projected on the retina, has the noteworthy advantage of significantly increasing the contrast of the image with respect to conventional solutions.

Preferably, the illuminator 12 comprises a second projection mask 122 that stops a portion of the light emitted by the light source 121.

The mask 122 is arranged so as to be optically conjugated with a region of the apparatus comprised between the separation diaphragm 161 and the scanning means 17, consequently being optically conjugated also with the pupil 102 of the eye 100, during the operation of the apparatus 500.

Advantageously, the second projection mask 122 has a construction similar (even if not necessarily identical) to the first projection mask 112 of the illuminator 11, described above.

Preferably, the projection mask 122 is positioned in proximity of the light source 121, in the case in which this source is extended, for example of LED type.

The projection mask 122 comprises at least a rectilinear edge. This rectilinear edge is optically conjugated with the boundary 1B of the section of the light beam 1 at the region comprised between the separation diaphragm 161 and the scanning means 17.

Preferably, the illuminator 12 also comprises a second collimating optics 123, positioned between the projection mask 122 and the projection diaphragm 124.

In the embodiment of FIG. 5, the apparatus 500 can comprise a confocal diaphragm 23 substantially identical to the one already described for the embodiment shown in FIGS. 1-4.

According to a preferred variant of embodiment (FIG. 6), the confocal diaphragm 23 comprises a first and second confocal opening 231, 251 having a shape similar to the one described with regard to the embodiment shown in FIGS. 1-4.

According to this embodiment, the confocal diaphragm 23 is movable with respect to the optical path 2A so that the confocal openings 231, 251 of the confocal diaphragm 23 can be inserted, one at a time, in the optical path 2A.

First actuation means 28 can be used to move the confocal diaphragm 23.

With reference to FIG. 6, the main characteristics of the confocal openings 231, 251 are now described with reference to their corresponding position of insertion in the optical path 2A.

The confocal opening 231 has substantially the same characteristics as the confocal opening already described with regard to the confocal diaphragm 23 in the embodiment shown in FIGS. 1-4.

The confocal opening 251 preferably has an elongated shape and variable width. Preferably, it extends along a corresponding main axis of extension.

Preferably, the confocal diaphragm 23 is arranged so that this axis of extension of the opening 251 crosses the optical axis O2 of the optical path 2A.

The confocal opening 251 comprises the ends 252, in distal position with respect to the optical axis O2, and a central portion 255, in proximal position with respect to the optical axis O2.

Preferably, the confocal opening 251 is centered on the optical axis O2.

Preferably, the ends 252 are arranged symmetrically with respect to the central portion 235.

The confocal opening 251 is shaped so as to have at least a portion of a width larger than the width of said confocal opening at the optical axis O2. In other words, the confocal opening 251 is shaped so that its width, at the central portion 255, is smaller than its width at least at a portion different from the central portion.

Preferably, the confocal opening 251 is shaped so that its width progressively increases with the distance from said second optical axis O2, advantageously according to a law of variation such as to make the brightness of the image of the retina 101 acquired with the acquisition means 27 more uniform.

Also the laws of variation of the width of the openings 231, 251 of the diaphragm 23 can differ from one another and be based on different calculation criteria. In any case, they are calculated in relation to the shape and sizes of the openings 1140, 1240 of the diaphragms 114 and 124.

An example of preferred operating method for the apparatus 500, in the embodiment of FIG. 5, advantageously comprises the following steps (not necessarily in the same order as below):

inserting the confocal opening 231 in the optical path 2A;
activating only the illuminator 11;
obtaining a preliminary series of infrared images of the retina 101;
performing any adjustments of the apparatus 500;
acquiring one or more infrared images of the retina 101;
deactivating the illuminator 11; and/or
inserting the confocal opening 251 in the optical path 2A;
activating only the illuminator 12;
acquiring one or more color images of the retina 101.

Figure 7:
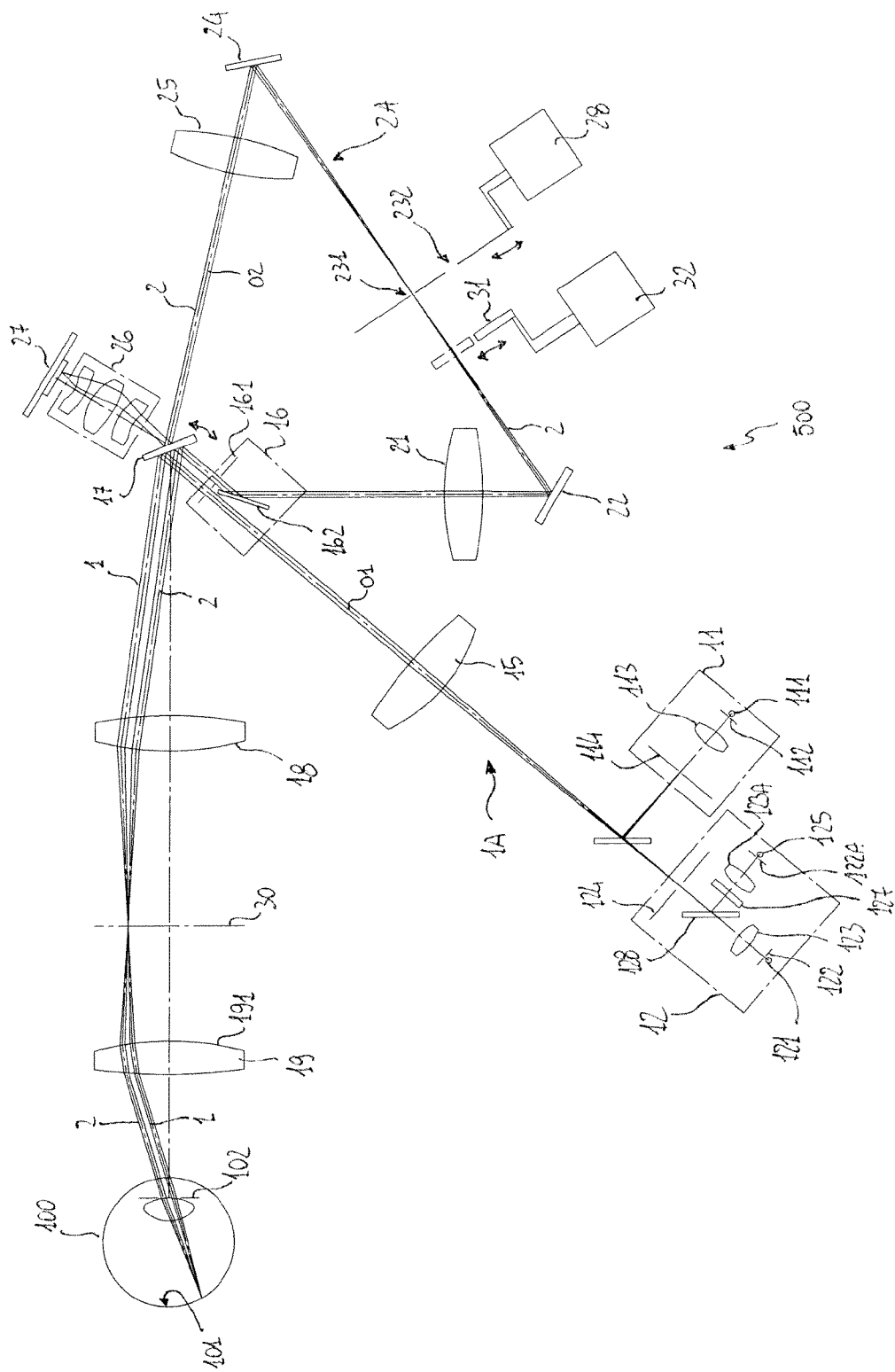
FIG. 7 schematically shows the eye examination apparatus according to the invention in a further embodiment thereof.

FIG. 7 shows a further embodiment for the apparatus 500. Many construction aspects of this embodiment of the apparatus 500 are substantially identical to the embodiment shown in FIG. 5. An important differentiation aspect consists in the fact that, in this embodiment, the illuminator 12 comprises a plurality of light sources 121, 125 capable of emitting light in different spectral bands.

The illuminator 12 preferably comprises a plurality of projection masks 122, 122A, each of which is operatively associated with a corresponding light source 121, 125.

The projection masks 122, 122A are preferably obtained in substantially the same way as the projection mask 112 described in relation to the embodiment of the FIGS. 1 and 2.

Therefore, each of them comprises at least a rectilinear edge capable of stopping a portion of the light emitted by the corresponding light source 121, 125.

The illuminator 12 preferably comprises a plurality of collimation optics 123, 123A, each of which is operatively associated with a corresponding light source 121, 125.

The illuminator 12 preferably comprises one or more dichroic mirrors 128 to direct (and optionally add together) the light produced by the light sources 121, 125 along the optical path 1A.

In the case in which the light sources 121, 125 are activated simultaneously, the illuminator 12 preferably projects white light.

In the case in which the light sources 121, 125 are activated separately, the illuminator 12 preferably projects colored light having a relatively small bandwidth.

Preferably, the light source 121 is adapted to emit light with wavelength comprised at least between 520 and 610 nm, while the light source 125 is adapted to emit blue light with peak wavelength comprised between 440 and 490 nm and with a bandwidth narrower than 40 nm.

Preferably, the light source 121 comprises a primary emitter that emits light with wavelengths below 500 nm and a mixture of phosphors adapted to convert at least a portion of the light emitted by said primary emitter in light having higher wavelengths.

Preferably, the aforesaid primary emitter consists of a first LED device that emits blue light, said first LED device having an emitting surface covered by the aforesaid mixture of phosphors.

The mixture of phosphors can be deposited as a layer directly on the surface of the semiconductor crystal of the first LED device.

Alternatively, the primary emitter can be a laser.

Preferably, the light source 125 comprises a second LED device that emits blue light.

Preferably, the illuminator 12 comprises a first filter 127 operatively associated with the light source 125 and positioned in fixed position.

Preferably, the filter 127 is positioned between the collimating optics 123A and the dichroic mirror 128.

Preferably, the apparatus 500 comprises a second filter 31 reversibly movable so as to be inserted/removed in/from the optical path 2A.

Second actuation means 32 can be used to move the filter 31.

When the second filter 31 is inserted in the optical path 2A and the light source 125 that emits blue light is activated, the apparatus 500 allows fluorescence or autofluorescence images to be obtained.

The production of an illuminator 12 with several light sources that can be added together by means of dichroic mirrors 128 has considerable advantages.

With respect to the solution comprising a single white light source (FIG. 5), it is in fact possible to increase the light power projected by the illuminator 12 in the case of simultaneous activation of the sources 121, 125.

On the other hand, it is possible to select a narrower range of wavelengths to illuminate the retina, in the case in which part of the sources 121, 125 are activated.

An example of preferred operating method for the apparatus 500, in the embodiment of FIG. 7, advantageously comprises the following steps (not necessarily in the same order as below):
inserting the confocal opening 231 in the optical path 2A;
activating only the illuminator 11;
obtaining a preliminary series of infrared images of the retina 101;
performing any adjustments of the apparatus 500;
acquiring one or more infrared images of the retina 101;
deactivating the illuminator 11;
inserting the confocal opening 251 in the optical path 2A; and/or
simultaneously activating the light sources 121, 125 to emit a flash of white light;
acquiring one or more color images of the retina 101;
deactivating the light sources 121, 125; and/or
inserting the filter 32 in the optical path 2A;
activating the light source 125 that emits blue light;
acquiring one or more fluorescence or autofluorescence images of the retina 101;
deactivating the light sources 121, 125;
extracting the filter 32 from the optical path 2A;
acquiring one or more red-free images of the retina 101.

In the case in which the illuminator 12 comprises a larger number of light sources (i.e. larger than 2), it is possible to activate these latter in series to obtain images of the retina in illumination conditions with narrow wavelength bands.

The apparatus 1 according to the invention has considerable advantages with respect to prior art. The use of projection diaphragms having openings of elongated shape with smaller width, at the central portion, and larger width, at least at a portion different from the central portion makes it possible to:
compensate for any lack of brightness in the peripheral regions of the images;
increase the signal/noise ratio in the peripheral regions of the images;
reduce the alignment criticalities of the diaphragm of the illuminator and of the confocal diaphragm;
obtain images with a wide field of view, even of around 60°.

The use of projection masks having at least a rectilinear edge makes it possible to:
define the shape and the size of the section of the illumination beam 1 at the level of the pupil of the eye without adding undesired reflections on the image;
reduce the section of the light beam generated by the light source eliminating, right from its emission, light not useful to illuminate the retina and that could cause undesired reflections.

The use of a plurality of illuminators, in particular of an illuminator that emits white light and an illuminator that emits infrared light, and of a movable confocal diaphragm with several confocal openings makes it possible to:
separately optimize operation of the apparatus with infrared and visible light;
improve performances with regard to contrast and brightness of the images and robustness against reflections;
separately perform the optical adjustments of the machine and in vivo observation of the retina, using infrared light that does not cause the pupil of the eye to close.

The use of a white light illuminator with several light sources that can be added together by means of dichroic mirrors makes it possible to:
increase the power density emitted by the white illuminator;
produce images of the retina illuminated with light in different wavelength ranges.

The use of a white light illuminator provided with a first filter that filters the light of one of the light sources and of a second filter on the optical imaging path to filter the light received by the retina makes it possible to obtain fluorescence and autofluorescence images.

The apparatus 500 has a very compact structure and is easy to produce on an industrial scale, with considerable advantages in terms of limiting production costs.

The invention claimed is:

1. An eye examination apparatus comprising:
an illuminator adapted to project a light beam along an optical illumination path having a first optical axis to illuminate the retina of an eye, said illuminator comprising a light source and a projection diaphragm adapted to shape the light beam projected by said illuminator, said projection diaphragm being optically conjugated with the retina during operation of said examination apparatus;
acquisition means adapted to receive light reflected by the retina along an optical imaging path having a second optical axis and to acquire images of the retina;
scanning means adapted to move the light beam projected by said illuminator on the retina along a scanning direction;

separation means of the light beams adapted to separate the light projected by said illuminator from the light reflected by the retina and directed toward said acquisition means;
wherein the projection diaphragm comprises at least a projection opening having an elongated shape and variable width, said projection opening comprising at least a portion having a width larger than the width of said projection opening at said first optical axis.

2. The eye examination apparatus of claim 1, wherein the projection opening is shaped so that its width progressively increases with the distance from said first optical axis between a minimum value, at said first optical axis, and maximum values, at ends of said projection opening or at portions proximate to said ends.

3. The eye examination apparatus of claim 1, wherein the illuminator comprises a projection mask adapted to stop a portion of the light emitted by said light source, said projection mask being optically conjugate with a region of said apparatus comprised between said scanning means and a separation diaphragm of said separation means of the light beams, said projection mask comprising at least a rectilinear edge.

4. The eye examination apparatus of claim 3, wherein the light beam projected by said illuminator does not cross portions of said separation diaphragm in the proximity of an opening of said projection diaphragm, through which light reflected by the retina passes.

5. The eye examination apparatus of claim 3, wherein the projection mask is positioned in the proximity of said light source.

6. The eye examination apparatus of claim 1, further comprising, along said optical imaging path, at least a confocal diaphragm optically conjugate with the retina during the operation of said apparatus, said confocal diaphragm comprising at least a confocal opening having an elongated shape and variable width, said confocal opening comprising at least a portion having a width larger than the width of said confocal opening at said second optical axis.

7. The eye examination apparatus of claim 6, wherein the confocal opening is shaped so that its width progressively increases with the distance from said second optical axis between a minimum value, at said second optical axis, and maximum values, at ends of said confocal opening or at portions proximate to said ends.

8. The eye examination apparatus of claim 1, comprising at least two separated illuminators, each illuminator comprising at least a corresponding light source and a corresponding projection diaphragm provided with at least a corresponding projection opening having an elongated shape and variable width, each projection opening comprising at least a portion having a width larger than the width of said projection opening at said first optical axis.

9. The eye examination apparatus of claim 8, wherein each projection opening is shaped so that its width progressively increases with the distance from said first optical axis between a minimum value, at said first optical axis, and maximum values, at ends of said projection opening or at portions proximate to said ends.

10. The eye examination apparatus of claim 8, wherein each illuminator comprises a corresponding projection mask adapted to stop a portion of the light emitted by said light source, each projection mask being optically conjugate with a region of said apparatus comprised between said scanning means and a separation diaphragm of said separation means of the light beams, each projection mask comprising at least a rectilinear edge.

11. The eye examination apparatus of claim 10, wherein the light beam projected by each illuminator does not cross portions of said separation diaphragm in proximity of an opening of said projection diaphragm, through which light reflected by the retina passes.

12. The eye examination apparatus of claim 8, wherein the confocal diaphragm comprises a first and second confocal opening having an elongated shape and variable width, and wherein at least a portion of each of said confocal openings, when inserted in said optical imaging path, have a width larger than the width of said confocal openings at said second optical axis, said confocal diaphragm being movable with respect to said optical imaging path so that said confocal openings can be inserted or removed, one at a time, in or from said optical imaging path.

13. The eye examination apparatus of claim 12, wherein each of said confocal openings, when inserted in said optical imaging path, is shaped so that its width progressively increases with the distance from said second optical axis between a minimum value, at said second optical axis, and maximum values, at ends of said confocal opening or at portions proximate to said ends.

14. The eye examination apparatus of claim 1, comprising an illuminator comprising at least two light sources that emit light in different spectral bands.

15. The eye examination apparatus of claim 14, wherein the illuminator comprises a first light source adapted to emit light with a wavelength at least comprised between 520 nm and 610 nm and a second light source adapted to emit blue light with a peak wavelength comprised between 440 nm and 490 nm and with a bandwidth narrower than 40 nm.

16. The eye examination apparatus of claim 15, wherein the first light source comprises a primary emitter that emits light with a wavelength lower than 500 nm and a mixture of phosphors adapted to convert at least a portion of the light emitted by said primary emitter in light having higher wavelengths.

17. The eye examination apparatus of claim 16, wherein the primary emitter comprises a first LED device that emits blue light, said first LED device having an emitting surface covered by said mixture of phosphors.

18. The eye examination apparatus of claim 15, wherein the second light source comprises a second LED device that emits blue light.

19. An eye examination method, comprising:
projecting a light beam from a light source along an optical illumination path having a first optical axis to illuminate the retina of an eye;
shaping the projected light beam via a projection diaphragm optically conjugated with respect to the retina, wherein the projection diaphragm comprises at least a projection opening having an elongated shape and variable width, said projection opening comprising at least a portion having a width larger than the width of said projection opening at said first optical axis;
acquiring images of the retina from light reflected by the retina along an optical imaging path having a second optical axis;
moving the light beam projected on the retina along a scanning direction; and
separating the projected light beam from the light beam reflected by the retina.

20. An eye examination apparatus comprising:
a light source adapted to project a light beam along an optical illumination path having a first optical axis to illuminate the retina of an eye, wherein the projected light beam is shaped by a projection diaphragm optically conjugated with the retina and comprising at least a projection opening having an elongated shape and variable width, and wherein the projection opening comprises at least a portion having a width larger than the width of the projection opening at the first optical axis;

one or more camera sensors adapted to receive light reflected by the retina along an optical imaging path having a second optical axis, and to acquire images of the retina;

one or more mirrors adapted to direct at least a portion of the light reflected by the retina along the optical imaging path toward the one or more camera sensors; and a separation diaphragm adapted to separate the light projected by said illuminator from the light reflected by the retina and directed toward the one or more cameras.

* * * * *